United States Patent
Mannella

(10) Patent No.: US 6,322,823 B1
(45) Date of Patent: Nov. 27, 2001

(54) PMS DEFENSE: AN AROMATHERAPY COMPOUND FOR THE RELIEF OF SYMPTOMS OF PREMENSTRUAL SYNDROME

(76) Inventor: Lenore C. Mannella, 177 Riverside Ave., STE F, Newport Beach, CA (US) 92663

( * ) Notice: Subject to any disclaimer, the term of this patent is extended or adjusted under 35 U.S.C. 154(b) by 0 days.

(21) Appl. No.: 09/322,319

(22) Filed: May 27, 1999

(51) Int. Cl.7 .................................................. A61K 65/00
(52) U.S. Cl. .......................... 424/725; 424/725; 424/736; 424/746; 424/778
(58) Field of Search ................................ 424/195.1, 725, 424/736, 746, 728

(56) References Cited

U.S. PATENT DOCUMENTS 3,637,533 * 1/1972 Dahill, Jr. .
3,852,219 * 12/1974 Nikawitz et al. .
5,565,199   10/1996 Page et al. .
5,707,630    1/1998 Morrow .

* cited by examiner

*Primary Examiner*—Leon B. Lankford, Jr.

(57) ABSTRACT

This invention is directed to an Aromatherapy compound to combat symptoms of Premenstrual Syndrome. It uniquely comprises an externally applied compound consisting of "essential oils" (highly concentrated oils extracted from plant cells for use in natural, therapeutic applications) that aid in the relief or reduction of symptoms of PMS. The compound preferably comprises equal proportions of essential oil of geranium, essential oil of clary sage, and essential oil of orange. The compound can be used "neat" (directly on the skin), however, the preferred embodiment is to add the compound to a "carrier" (a base for diluting the Aromatherapy compound) such as lotion or vegetable oil. The preferred formula is approximately 3 milliliters essential oil (1milliliter of geranium, 1 milliliter of clary sage, and 1 milliliter of orange) blended in 120 milliliters of carrier.

8 Claims, No Drawings

PMS DEFENSE: AN AROMATHERAPY COMPOUND FOR THE RELIEF OF SYMPTOMS OF PREMENSTRUAL SYNDROME

BACKGROUND

1. Field of the Invention

This invention is directed to an Aromatherapy compound using a unique combination of natural oils extracted from plant cells to combat symptoms of Premenstrual Syndrome.

2. Description of Prior Art

PMS symptoms result from the fluctuation of hormones accompanying the female menstrual cycle. Symptoms include, but are not limited to, water retention, cramping, breast pain, and mood swings.

Natural health care companies supply female consumers with a variety of products that purportedly reduce symptoms of PMS. These products may be in the form of vitamin supplementation or herbal compounds, as in U.S. Pat. No. 5,707,630 to Morrow (1998), and more broadly cite relief of ". . . PMS through menopausal symptoms.".

U.S. Pat. No. 5,565,199 to Page & Rector-Page (1996), provides a method of synthesizing natural substitutes for progesterone and estrogen from herbaceous plants, and is taken in capsule form or applied topically. This product targets hormonal replacement associated with menopausal symptoms.

Since herbal supplements require time to reach therapeutic levels in the body, the supplements must be taken consistently, sometimes over a period of months, before results are obtained. Additionally, most of these natural supplements do not specifically address relief of breast pain associated with PMS.

Advantages

Several advantages to the invention, PMS Defense, are as follows:

(a) PMS Defense is unique in the use of a natural essential oil based aromatherapy compound for the relief of PMS symptoms.

(b) PMS Defense blends essential oils of geranium, clary sage, and orange, for their diuretic, antispasmodic, and antidepressant properties (among other important functions as described in greater detail in the remainder of this report).

(c) Borage oil is used as a carrier in the extra strength version for it's high levels of gamma linolenic acid (GLA). GLA assists the body in manufacturing prostaglandins, which aid the body in combating pain and inflammation, and help regulate the menstrual cycle.

(d) PMS Defense directly targets breast pain (applied directly to the breasts and abdominal areas).

(e) PMS symptoms are relieved in a much more rapid timeframe than traditional natural remedies.

(f) PMS Defense is applied topically in a lotion or oil base; crucial for individuals who find it difficult to tolerate supplements, or swallow capsules.

(g) PMS Defense is applied just prior to the onset of the Menstrual Cycle (whenever the user normally begins to experience symptoms). It need not be used on a daily basis.

(h) PMS Defense is as pleasant and easy to use as body lotion.

SUMMARY

PMS Defense is a unique, easy to use, natural remedy for relieving symptoms of PMS. The preferred blend comprises essential oils of geranium, clary sage, and orange, in equal proportions of approximately 1 milliliter each per 120 milliliters of a lotion or oil carrier, which is applied topically to the breasts and abdomen.

DESCRIPTION OF PREFERRED EMBODIMENT(S)

As noted above, in the preferred embodiment, the essential oil blend comprises essential oil of geranium, essential oil of clary sage, and essential oil of orange, in equal proportions of approximately 1 milliliter each per 120 milliliters of carrier.

Some relevant properties of essential oils in general, and more specifically as it relates to the essential oils used in PMS Defense are as follows:

Antidepressant (mood elevators)—geranium, clary sage and orange.

Antispasmodic (muscle cramps)—orange.

Diuretic (water retention)—geranium.

Emmenagogue (encourages menstruation)—clary sage.

Hormone balancing—geranium.

Sedative (calming effect on the nervous system)—clary sage.

Stimulant (increases body activity generally, or of a specific organ)—geranium.

Tonic (general body strengthening, or of a specific organ)—geranium.

Essential oil of geranium or Pelargonium Odorantissimum, is distilled from the leaves of the plant. Its principal constituents include geraniol, citronellal, linalol, terpineol and alcohols. Essential oil of geranium is an adrenal cortex stimulant and has a balancingeffect on the body. Since hormones secreted by the adrenal cortex are primarily regulators of hormones secreted by other organs, including sex hormones, it is extremely effective in conditions where hormones fluctuate, as in the female menstrual cycle and menopause. Essential oil of geranium is a natural diuretic, which is particularly helpful in eliminating excess fluid retention commonly associated with PMS. It also has antidepressant and calming qualities, which may assist in easing mood swings.

Essential oil of Clary Sage or *salia sclarea*, is distilled from the flowers and flower tips of the plant. Its principal constituents include borneol, salviol, cineol, sclareol, salvene and salvone. Clary Sage is one of the most powerful relaxants available in Aromatherapy, has antidepressant qualities, and is effective in relieving stress and tension. More importantly, it has strong antispasmodic properties, which is particularly helpful in relieving uterine contractions that cause pain and cramps during the menstrual cycle.

Essential oil of Orange or *citrus auranlium*, is extracted by applying pressure to the outer part of the peel. Its principal constituents include limonene, citral, and citronellal. It has antispasmodic, antidepressant and mildly sedative qualities that are effective in easing cramps, mood swings, and anxiety associated with PMS.

Borage oil or *borago officinalis*, with its high levels of Gamma Linolenic Acid (GLA), is used as a carrier in the extra strength version. GLA is an essential fatty acid that the body uses to manufacture prostaglandins (hormone-like substances). Prostaglandins, which some people are unable to make in sufficient quantities for their body's needs, are important to the healthy function of body tissue, and assist the body in combating pain and inflammation, and regulating the menstrual cycle.

Conclusions, Ramifications, and Scope

Accordingly, the reader will see that PMS Defense has several unique advantages over traditional natural remedies for PMS, including:

- Use of an essential oil blend that specifically addresses PMS symptoms.
- Ability to target breast pain (applied directly to the breasts and abdominal areas)
- Faster timeframe to relieve symptoms than traditional natural remedies.
- Ease of use; topical application in a lotion or borage oil base.
- Need not be used on a daily basis.

Although the descriptions in the above paragraphs contain much specificity, these should not be construed as limiting the scope of the invention, but merely as illustrating the presently preferred method of creating PMS Defense. For example, borage oil may be added as an additional ingredient to a lotion base, as opposed to a substitute, along with the essential oil blend, to comprise an extra strength lotion version. The blends may also be added to other carriers, such as bath oils, as an alternative approach to delivery of the active ingredients. Thus the scope of the invention should be determined by the appended claims and their legal equivalents, rather than solely by the examples given.

What is claimed is:

1. A composition consisting of essential oil of geranium, essential oil of clary sage, essential oil of orange and a carrier.

2. A topical composition comprising a carrier and equal proportions of essential oil of geranium, essential oil of clary sage, essential oil of orange.

3. A composition comprising essential oil of geranium, essential oil of clary sage, essential oil of orange and borage oil.

4. The composition of claim 1 or 2 or 3 wherein each essential oil is present in the amount of 1 ml and the carrier is present in the amount of 120 ml.

5. The composition of claim 3 wherein each essential oil is present in the amount of 1 ml and the borage oil is present in the amount of 120 ml.

6. The composition of claim 1 or 3, wherein each essential oil is in equal proportions.

7. The composition of claim 6 wherein the carrier is a lotion.

8. The composition of claim 1, 2 or 3, wherein said carrier is a lotion.

* * * * *